United States Patent
Pasanen

(10) Patent No.: US 9,884,834 B2
(45) Date of Patent: Feb. 6, 2018

(54) COMBINED LEVULINIC ACID AND FURFURAL PRODUCTION FROM BIOMASS

(71) Applicant: Neste Oyj, Espoo (FI)

(72) Inventor: Antti Pasanen, Espoo (FI)

(73) Assignee: NESTE OYJ, Espoo (FI)

( * ) Notice: Subject to any disclaimer, the term of this patent is extended or adjusted under 35 U.S.C. 154(b) by 0 days.

(21) Appl. No.: 15/388,538

(22) Filed: Dec. 22, 2016

(65) Prior Publication Data

US 2017/0183322 A1 Jun. 29, 2017

(30) Foreign Application Priority Data

Dec. 23, 2015 (FI) .................................. 20156010

(51) Int. Cl.
*C07D 307/50* (2006.01)
*C07C 51/00* (2006.01)

(52) U.S. Cl.
CPC ............ *C07D 307/50* (2013.01); *C07C 51/00* (2013.01)

(58) Field of Classification Search
CPC .............................. C07D 307/50; C07C 51/00
USPC .......................................... 549/489; 562/515
See application file for complete search history.

(56) References Cited

U.S. PATENT DOCUMENTS

| | | | |
|---|---|---|---|
| 2,813,900 A | 11/1957 | Dunlop et al. | |
| 3,701,789 A | 10/1972 | Ramos-Rodriguez | |
| 4,533,743 A | 8/1985 | Medeiros et al. | |
| 4,897,497 A | 9/1990 | Fitzpatrick | |
| 5,608,105 A | 3/1997 | Fitzpatrick | |
| 6,617,464 B2 | 9/2003 | Manzer | |
| 2012/0083611 A1 | 4/2012 | Van Buljtenen et al. | |
| 2012/0329981 A1 | 12/2012 | Castelijns et al. | |
| 2013/0168227 A1 | 7/2013 | Fagan et al. | |
| 2015/0080602 A1 | 3/2015 | Kelly et al. | |
| 2016/0076112 A1 | 3/2016 | Cai et al. | |

FOREIGN PATENT DOCUMENTS

| | | |
|---|---|---|
| CN | 101805316 A | 8/2010 |
| CN | 102558108 B | 7/2012 |
| CN | 102659723 A | 9/2012 |
| CN | 102617519 B | 8/2014 |
| EP | 2 537 841 A1 | 12/2012 |
| EP | 2 537 840 B1 | 7/2013 |
| WO | WO 89/10362 A1 | 11/1989 |
| WO | WO 2014/176531 A2 | 10/2014 |

OTHER PUBLICATIONS

Finnish Search Report dated Apr. 22, 2016 and, issued by the Finnish Patent and Registration Office in the corresponding Taiwanese Patent Application No. 20156010. (2 pages).

Extended European Search Report dated Feb. 3, 2017, by the European Patent Office in corresponding European Patent Application No. 16204224.6. (11 pages).

(Continued)

*Primary Examiner* — T. Victor Oh
(74) *Attorney, Agent, or Firm* — Buchanan Ingersoll & Rooney PC

(57) ABSTRACT

A process is provided for improved levulinic acid production form biomass, wherein furfural is recovered from vapor flow from the levulinic acid production reactor. The reaction conditions can be chosen to enable good yield for both products and minimization of undesired side products.

12 Claims, 1 Drawing Sheet

(56) References Cited

OTHER PUBLICATIONS

Lange et al: "Furfural-A Promising Platform for Lignocellulosic Biofuels", Chemsuschem, vol. 5, No. 1, Jan. 9, 2012 (Jan. 9, 2012), pp. 150-166, XP055338725.
Yan et al. "Synthesis of y-Valerolactone by Hydrogenation of Biomass-derived Levulinic Acid over Ru/C Catalyst" Energy Fuels, 2009, vol. 23, No. 8, pp. 3853-3858.
Chalid et al. "Green polymer precursors from biomass-based levulinic acid", SciVerse ScienceDirect, Procedia Chemistry 4 (2012), pp. 260-267.
Search Report dated Apr. 4, 2016, by the Finnish Patent Office in corresponding Finnish Patent Application No. 20156006. (2 pages).

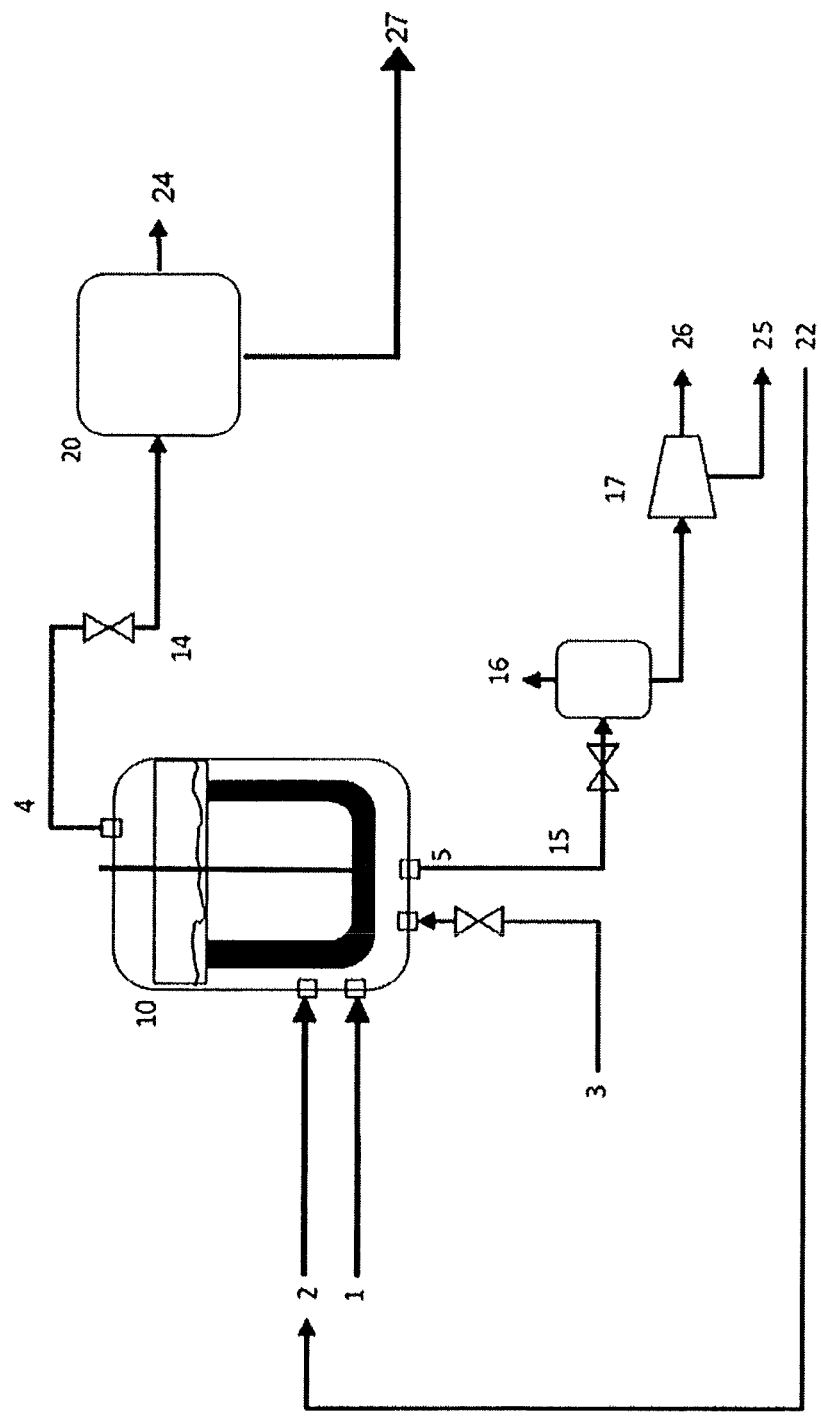

COMBINED LEVULINIC ACID AND FURFURAL PRODUCTION FROM BIOMASS

RELATED APPLICATION

This application claims priority under 35 U.S.C. § 119 to Finnish Patent Application No. FI 20156010 filed in Finland on Dec. 23, 2015, the entire content of which is hereby incorporated by reference in its entirety.

FIELD

The disclosure generally relates to conversion of biomass based feedstock into components classifiable as renewable, such as renewable vehicle fuel components. For example, but not exclusively, a process for combined levulinic acid and furfural production is disclosed. For example, but not exclusively, a combined levulinic acid and furfural reactor are disclosed.

BACKGROUND INFORMATION

Levulinic acid has been identified as a suitable chemical feedstock that may be processed from hexoses derived from biomass.

U.S. Pat. No. 2,813,900 discloses a process for continuous levulinic acid production. In this process the feed is biomass from which pentoses have first been recovered, more specifically the feed is a residue from a furfural process. The process is based on acid hydrolysis, wherein the cellulose polymers are degraded into hexose monomers in the first reactor, and reaction from hexoses to levulinic acid in second reactor, which is an elongated horizontally disposed chamber designed to create turbulence to the flow.

U.S. Pat. No. 5,608,105 discloses a process wherein carbohydrate feedstock and sulfuric acid catalyst solution are mixed, and the slurry is supplied continuously to a tubular reactor. This reactor is operated at an exemplary temperature of 210-220° C. in order to hydrolyse the carbohydrate polysaccharides into their soluble monomers (hexoses and pentoses). This hydrolysis reaction is rapid after which the outflow of the first reactor is fed to a continuously stirred tank reactor operated at a lower temperature (190-200° C.) with a longer residence time of 20 min. Levulinic acid is removed by drawing-off liquid from the second reactor. Solid by-products are removed from the levulinic acid solution in a filter-press unit.

Various processes for furfural production have been suggested. When aiming at low investment and low operating costs, production may be based on organic acids formed from biomass intrinsically by heating. Such a process is relatively slow and for example, allows furfural recovery only. To further develop the effectiveness and speed up the conversion, an acid catalyst may be added to the process to replace or act together with naturally occurring organic acids.

US Patent Publication No. US2013/0168227 discloses a process for furfural production from biomass, such as corn cob, bagasse and bamboo. In this method, initially biomass, acid catalyst, sulfolane as a water miscible solvent, and water were fed into the reactor. The furfural formed together with water, forming an azeotropic mixture, were distilled off leaving the solvent and residual side products, such as levulinic acid in the reactor. Humins and lignin which are soluble in sulfolane, were precipitated by addition of water and separated from side products.

Hence, there is a need to simplify the process of levulinic acid production. Another need is to convert biomass into levulinic acid and furfural in a more effective way. There is a further need to optimize the yield of both levulinic acid and furfural as reaction products. A combined process for conversion of hexoses and pentoses to levulinic acid and furfural respectively is therefore disclosed. Exemplary embodiments can improve both levulinic acid and furfural recovery in the process.

SUMMARY

A process is disclosed for converting biomass into levulinic acid and furfural in one reactor, wherein process conditions in the reactor comprise: temperature from 150 to 200° C.; residence time at said temperature from 30 to 480 min; $H_2SO_4$ content from 1 to 5%-wt of the feed; and continuous steam stripping.

BRIEF DESCRIPTION OF THE DRAWING

Exemplary embodiments of the present invention will be described, by way of example, with reference to the accompanying drawing, FIG. 1, which shows a simplified view of a process example flow diagram and mass balance of the present process.

DETAILED DESCRIPTION

According to a first aspect of the disclosure there is provided a process for converting biomass into levulinic acid and furfural in one reactor, wherein the process conditions in the reactor include:
temperature from 150 to 200° C.;
residence time at the temperature from 30 to 480 min;
$H_2SO_4$ content 3-5%-wt of the feed;
continuous steam stripping.

An aim is to react both hexoses and pentoses present in the feed biomass. In the present process, the reactor conditions are selected to enable reactions to yield levulinic acid and furfural from this one reactor without need for two separate reactors with different reaction conditions, such as temperature. When applying steam stripping the sparged water vapor takes effectively furfural into gas phase.

According to a preferred exemplary embodiment of the present process the conditions in the reactor further include one or more of parameters selected from:
a pressure from 3 to 14 bar;
mixing;
dry matter from 5 to 30%-wt, preferably, for example, from 15 to 20% of the feed.

The process may further include recovery of the levulinic acid from the aqueous phase (slurry) of said reactor either continuously or batch-wise. The process may further include recovery of the furfural from the vapor flow of said reactor. The inventor has surprisingly found that these process conditions allow reactions, wherein hexose and pentose monomers react to levulinic acid and furfural respectively in one reactor. According to one embodiment, wherein the starting material in the feed includes oligo or polysaccharides, such as lignocellulosic biomass, the glycosidic bonds between sugar monomers are first hydrolyzed to depolymerize carbohydrate chains, and then the released hexoses and pentoses reacted in one reactor according to the present process.

In the experimental part, certain benefits have been shown using lignocellulosic biomass.

The method may further include processes wherein levulinic acid obtained by the present process is further converted to products thereof, such as resins, plasticizers, speciality chemicals, herbicides or a fuel extender.

Different embodiments disclosed herein will be illustrated or have been illustrated only in connection with some select aspects disclosed herein. A skilled person will appreciate that any embodiment of an aspect disclosed may apply to other aspects disclosed herein.

Levulinic acid produced from biomass has shown to act as a promising precursor for several biobased compounds. Levulinic acid is a reagent often used to improve of modify solubility, plasticity, moldability, etc. properties in different applications. In addition to levulinic acid itself, esters thereof and gamma valerolactone are especially interesting compounds derivable thereof. The hexoses abundant as different polymers and oligomers in nature may be converted to levulinic acid via a simple reaction. From one mole of hexose, one mole of both levulinic acid and formic acid is produced. Said reaction may be catalyzed by acid. The reaction is given as "reaction 1" below:

Preferably, for example, acid is supplied to the reactor. It can either be impregnated to the biomass feed, mixed with added water, fed directly into the reactor, preferably, for example, diluted, or any combinations thereof. Many acids suitable to catalyze reactions taking place in the present process are known. Mineral acids, such as HCl, $H_3PO_4$ and $H_2SO_4$ are preferred in exemplary embodiments since they tolerate high temperature and other process conditions better than organic acids, such as carboxylic acids. It is beneficial to use acids, which are not evaporated under reactor conditions. Some metals and salts, such as $FeCl_2$ are also known to catalyze above reactions 1 and 2.

The present process benefits from the multipotency of acid catalyst under present conditions. Acid hydrolysis of glycosidic bonds between sugar monomers, hexoses, pentoses and combinations thereof, is a rapid reaction. Since inorganic acids often used are sterically small they reach sites all over the biomass carbohydrate structures. As hydrolysis proceeds, and the polymeric biomass is degraded into smaller polymeric or oligomeric units, the cleavage of glycosidic bonds makes bonds easier to access, enhances

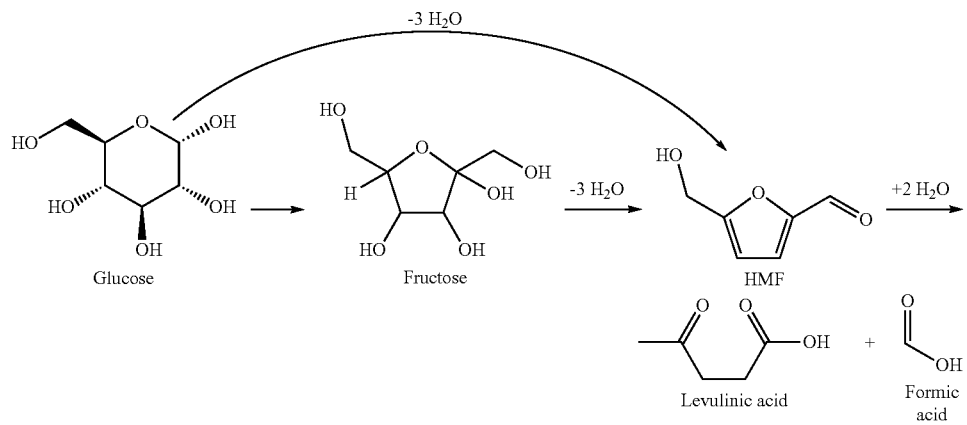

Reaction 1.

Another reaction converting biomass sugar components into biobased compounds is the reaction of pentoses into furfural. Furfural is an easily volatile compound at the present reaction conditions. Reaction through which pentoses are converted into furfural given as "reaction 2" below.

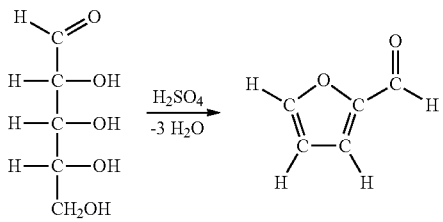

Reaction 2.

In the literature, some processes wherein acid is not added are published. These processes are based on activity of the acids formed as products from the reactions. Nevertheless, the reaction initiation is slow and residence times may be long without added acid. Removal of acids (e.g formic acid) during the process may not therefore seem attractive.

solubility to aqueous medium and thereby contributes to process rheology; mixing of the slurry, material transfer, removal of volatile compounds from the slurry etc. As shown in above reactions 1 and 2, the acid catalyst also contributes to the formations of both levulinic acid and furfural.

Use of sulfuric acid, $H_2SO_4$, as the catalyst, has proven to be preferable for exemplary embodiments of the present process. It is non-volatile, sterically relatively small and very effective. The amount of sulfuric acid in reaction slurry is a balance of tolerable corrosion and reaction rate. However, since it is not consumed in the reaction, choice of other reaction parameters may balance the need for high concentration. Since the reactions catalyzed by sulfuric acid under the present process conditions produce water, this should be taken onto account when calculating the balances. The condensation from steam stripping also may dilute the slurry and hence lower sulfuric acid concentration. The amount in the input to the reactor may vary between 1 to 10%-wt, but preferably is, for example, from 1 to 5%-wt of the sulfuric acid calculated in relation to the total mass of the feed thereto. After reaction, sulfuric acid is recoverable from the slurry and reusable in the process.

The chemical composition of natural biomass depends on its source. Generally lignocellulosic biomass consists of 38-50% of cellulose, 23-32% hemicellulose and 15-25% (dry weight) lignin. It may further contain other components, for example starch, which is an equally useful hexose source. Cellulose is a non-branched water-insoluble polysaccharide consisting of several hundred up to tens of thousands of glucose units. With depolymerization it yields glucose oligomers and eventually hexoses, also known as C6 sugars. Cellulose is the most abundant biopolymer synthesized by nature. Hemicellulose has, for example, lower molecular weight than cellulose. Hemicellulose is a polymeric material, often branched, comprising both hexoses (glucose, mannose and galactose) and pentoses (mainly arabinose and xylose). The third major component in lignocellulosic biomass, lignin is a highly cross-linked polymer made from substituted phenylpropene units.

In the context of this disclosure, biomass may refer to material directly obtained from natural sources, i.e. natural biomass, or may optionally be pretreated. For Example, a process is adapted according to type and properties of the biomass used, but variation and mixing of biomasses from different sources is applicable. Such pretreatments include but are not limited to washes, grinding, crushing, milling etc. Exemplary sources for biomass are also waste streams from different biomass utilizing processes. Suitable waste streams which may be used in the feed of the present process include but not limited to like bagasse, straw, solid recovered fuel (=commercial and industrial package waste), forest residue, and so on. In embodiments wherein the biomass is considered waste or recycled from another process, environmental benefits may be found. Most preferred environmentally and ethically are embodiments wherein the biomass has no alternative use and is not suitable for food production.

When using solid feed biomass in the present process the biomass feed material is preferably, for example, crushed into particle mean diameter from 0, 5 to 10 mm, more preferably, for example, from 1 to 2 mm. The reactions 1 and 2 are partly mass transfer limited and particle size of from 1 to 2 mm provides feasible yields and rates especially when woody and straw feed biomass is used.

The present process provides unexpected benefits when the biomass includes at least cellulose and hemicellulose. Alternatively it may, for example, cellulose and hemicellulose which have been treated prior to this process. Exemplary pretreatments include treatments which are chemical, biochemical, mechanical or combinations thereof. Common pretreatments include but are not limited to soaking, swelling, softening to improve permeability, mechanical particle size diminishing and hydrolysis, by enzymes or acids.

Best results with embodiments of the present process may be obtained when the biomass treated according to the present process includes both hexoses and pentoses or precursors therefor, with the hexose:pentose ratio being from 33:1 to 1:2.

Within the context of the present disclosure, monosaccharides derivable from plant material, the carbon backbone of which consists of 5 carbon atoms, and which include at least two hydroxyl groups, are here referred to as pentoses. They are often also referred to as C5 sugars. Exemplary pentoses present in plants vary depending on the species, season, growth conditions etc. However, considering the present process, the exact composition is not critical. Monomers of pentoses are, for example, linked to same or other sugar monomers forming oligomers or polymers. Hydrolysis of bonds in between pentose units releases monomers, which may be processed according to the present process.

As used herein, a pentose source refers to material from which pentose monomers may be derived. Such sources include in addition the materials including pentoses as such, also the polymeric and oligomeric derivatives wherein said pentose monomers are linked to the same or different sugar monomers. For example in case of xylose, the corresponding polymeric derivative is xylan and the oligomers xylo-oligomers.

Whenever referring to the "feed" in this description, it is considered to include at least fed water, biomass and sulfuric acid, fed together or separately, needed in the reaction. However, the stripping steam is not included in this total even though some of the steam may condensate and increase the water content of the slurry. If a weight percentage of this feed is defined, the amount of individual component is compared to said total mass. For example the amount of sulfuric acid is given as from 1 to 5%-wt of the feed, wherein it is compared to the total of water, biomass and sulfuric acid fed to the process. Within the present disclosure, the flow of the feed or the catalyst are not critical. Hence, feed and catalyst may be supplied to the reactor continuously, semi-continuously or batchwise.

The dry matter content of the feed refers to the ratio between total liquids (sum of at least water and sulfuric acid-water solution) to solid matter fed into the reactor. In cases where the biomass feed have been subject to a pre-treatment, said solid matter, for example, contains some water and this is added up to the total water content. Those skilled in the art will appreciate, different means are available by which a slurry is obtainable. According to one embodiment, said liquids and solid matter are fed separately to the reactor. Another option is to use some of the water and/or sulfuric acid for pretreatment, for example by spraying the biomass and feeding moist or wet biomass and rest of the liquids separately. Another option is to mix all water or all water and sulfuric acid prior to the reactor and feeding the slurry into the reactor.

The dry matter content of said slurry may vary from about 5 to about 30%-wt and more preferably, for example, from about 15 to 20%-wt of the total slurry mass calculated based on feed. Most preferably the dry matter content is, for example, about 20%-wt of the total slurry mass calculated based on feeds. The dry matter content of about 20%-wt is surprisingly high when compared to dry matter contents of typical levulinic acid production processes, where dry matter content of 5-10%-wt is suggested. High dry matter content contributes to process economy.

In the reactor, there are two main phases which have their own inlets and outlets: the vapor phase and the aqueous slurry. Discussing the present process, the aqueous phase i.e. aqueous slurry refers to non-vaporisable components in the reactor staying slurried or dissolved in water under present reaction conditions. Such components include at least sulfuric acid, biomass and some derivatives thereof, especially levulinic acid and a part of formic acid. The vapor flow refers to components which are or become volatile under present reaction conditions. Vapor flow include at least the stripping steam, furfural and formic acid.

Based on characteristics of compounds present in the reactor, they remain in the aqueous slurry, vaporize and flow off with the gaseous phase of the reactor or are divided between the two phases. Exemplary components of the slurry are all the solid components either of the feed (biomass prior to degradation) or formed through reactions in the reactor, such as humins. The slurry is also referred to as the aqueous phase, because the main solvent and carrier is water in liquid form. However, water is present also in the vapor flow, where steam acts as the main carrier and stripping means.

According to an exemplary preferable embodiment, water is the only solvent added to the reactor and reactions are carried out in aqueous environment. As such, solvent free processes are desirable. Using water as the sole solvent, the present process provides further benefits for both running the operations and the equipment avoiding possible handling, recovery and recycling of second or further solvents in the system.

The biomass fed into the reactor is, for example, first solid, before saccharide polymers are degraded. However, as the sugar chains shorten as a result of acid catalysis, the solubility in water increases. Not even the monomers released are easily volatile, but remain in the slurry and there have a good contact with the catalyst. Further, the levulinic acid formed by conversion of hexoses remains dissolved in the aqueous phase as well under present reaction conditions.

As explained, converting one mole of hexose monomer into one mole of levulinic acid produces one mole of formic acid as a side product. Under the reactor conditions formic acid is somewhat volatile and is divided between aqueous and vapor flows. Due to partial pressure balances, more formic acid may be released from the slurry with continuous stripping than would be possible by methods only venting some of the vapor flow or releasing it into following flash tank. This provides further benefits in comparison to present levulinic acid processes. Firstly, the removal of one of the reaction product speeds up the process based on basic principles of reaction balances. Secondly, since the amount of formic acid dissolved in the aqueous phase is lower, the separation steps later on benefit from this balance.

Hence, at least formic acid and water are divided to both phases (vapor and slurry). Water acts as solvent and dispersant in the aqueous phase or slurry and on the other hand, as carrier gas in the vapor flow. Part of the formic acid vaporizes and is removed from the reactor via gas phase while part of the formic acid remains dissolved in the aqueous part. The experiments conducted to study the present process show that about 20-25% of the formic acid formed during the reaction flows out of the reactor carried by the stripping steam and about 70-80% remain in the slurry. This is a considerable relief to the levulinic acid recovery from the slurry. In reference reaction, where conditions were otherwise the same, but the reactor was not provided with steam stripping, all formic acid remained in the slurry.

The process parameters are optimized to allow sufficient residence time to convert the hexoses present in the aqueous phase of the reactor into levulinic acid. It has been experimentally defined that preferred residence time is at least 30 min. However, too long a residence time may lead to formation of undesired side products. It must also be considered that reactor time is a cost factor, which preferably is only as long as necessary. Therefore the preferred residence time at the temperature from 150 to 200 ° C. is, for example, between 30 and 480 min, more preferable, for example, between 60 to 240 min, and most preferably, for example, between 60 to 120 min.

According to one embodiment, the process is continuous and the sufficient residence time is provided by reactor design.

According to another embodiment the process is semi-continuous, wherein the aqueous phase is treated batch-wise, feeding the biomass, water and sulfuric acid into the reactor and emptying the slurry substantially at once after desired time. The residence time needed for levulinic acid production may thus be controlled by routine means of batch production. However, the steam stripping is conducted continuously over the entire stay of the biomass in the reactor.

It is essential for embodiments of the present disclosure to adjust the conditions in a way to create a continuous gas stream removing the furfural from the reactor as soon as possible after its formation. Therefore the steam entering the reactor must be selected in a way to enable at least part of it leaving the reactor in gas phase. In other words, it should not entirely be condensated in the process.

To meet these requirements, following alternatives are available.

The present inventor has found that a preferable exemplary weight ratio between stripping steam and dry matter fed in the reactor is from 5:1 to 1:3, preferably, for example, from 3:1 to 1:2 and most preferably, for example, about 1:1.

The steam temperature is preferably, for example, at saturated balance pressure at least 10° C., and more preferably, for example, at least about 20° C. higher than the reactor temperature.

According to another embodiment, the superheated stripping steam is used, said superheated steam having a lower pressure than the saturated balance pressure and higher than the reactor pressure.

Creating a continuous steam flow through the reactor has been shown to enhance the recovery of furfural in the experimental part of the present description. Without being bound to theories, rapid removal of furfural from the reactor conditions is believed to contribute to decreasing the loss of furfural to side products. Said side product formation is described for example in U.S. Pat. No. 4,533,743.

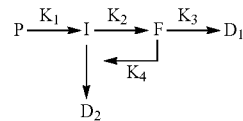

where:
P represents pentose
I a pentose-furfural intermediate
F furfural
$D_1$ and $D_2$ decomposition products
$K_1$, $K_2$, $K_3$ first order reaction rate constants
$K_4$ second order reaction rate constant
The intermediate I, has not been isolated or identified, because once formed, it disappears very rapidly (i.e. $K_2 >> K_1$).

The present inventor has surprisingly found that stripping the levulinic acid reaction slurry continuously with steam contributes to recovery of furfural. Furfural is thereby rapidly removed from the acidic reactor conditions and condensated from vapors. According to present knowledge, no recovery of furfural from the vapor flow from levulinic acid production has been reported. Even though, some vent gas in the prior art processes has been removed from the reactor converting hexoses into levulinic acid flashing the released gas phase, such exit from the reactor does not enable recovery of furfural. Said conditions are detrimental to furfural, which reacts to undesired side products and self-polymerizes. Furthermore, removal of furfural and other compounds volatile under reactor conditions is believed to advance the levulinic acid reactions. Hence, both conversions benefit in a synergistic way unforeseen based on prior art for either process.

Process Setup

With reference to attached FIG. 1 an embodiment of the present process is herein provided. In the following description, like numbers denote like elements. It should be appreciated that the illustrated figures are not entirely in scale, and that the figures mainly serve the purpose of illustrating exemplary embodiments of the invention.

In FIG. 1, the basic setting for the reaction is given. Levulinic acid reactor feed (1) including biomass and water, is fed into the reactor (10). Water may be mixed with feed material (1) or catalyst (2) before reactor (10) or both, in order to meet the applicable consistency in the reactor (10), preferably, for example, about from 65 to 75% water in reactor (10). Levulinic acid reaction catalyst (2), $H_2SO_4$, is fed into the reactor (10). Catalyst (2) may be fresh, diluted $H_2SO_4$, re-circulated from levulinic acid purification process or a combination thereof. Feed material (1) and catalyst (2) may be pre-mixed before the reactor (10). Levulinic acid reactor (10) is supplied with steam, called as stripping steam (3). The mass flow of stripping steam (3) depends on the feed biomass (1) and catalyst (2) temperature and reactor (10) temperature. Stripping is arranged countercurrent to the slurry flow direction in the reactor. For example, the ratio 1:1 for stripping steam and reactor feed dry matter may be used when feed biomass (1) and catalyst (2) temperatures are about 130° C. and the reactor (10) temperature is 180° C. It is routine optimization for a skilled person to find other process condition combinations changing feed biomass (1), catalyst (2), reactor (10) and steam (3) temperatures to provide about 80% of steam (3) to flow through the reactor with steam (3) to feed biomass (1) ratio of about 1:1.

Stripping steam (3) temperature is about from 10° C. to 20° C. higher than the reactor (10) temperature. Pressure of stripping steam (3) is saturated balance pressure or if using superheated steam then lower than saturated balance pressure but still higher pressure than reactor (10) pressure. The purity requirements for the stripping steam allow the steam used to be also recovered process steam or normal relatively pure process steam. However, the stripping steam should be relatively clean from furfural in order to recover the furfural effectively. With this arrangement, the formed furfural is mainly (>90%) transported with the stripping steam and recovered with vapor flow via outlet and vapor stream (4). For the recovery on furfural it is advantageous to recover it rapidly after its formation and remove it from process conditions in reactor (10). However, some furfural remains in reactor output flow (5). Levulinic acid and 5-hydroxymethyl furan do not evaporate with vapor stream, but leave the reactor in aqueous phase, as a slurry, through output flow (5).

A vapor flow (4) is taken continuously from the reactor gas phase. Vapor flow (4) recovers the formed furfural instantly as it is formed. Levulinic acid and 5-hydroxymethylfurfural remains completely in the reactor (10) solution and are taken out within the reactor output flow (5) for recovery and purification. Most of the formic acid formed is also recovered within the flow (3) and about 20-25% of the formed formic acid is evaporated into vapor flow (4). The vapor flow (4) and reactor (10) pressure are controlled with a valve (14). In order to enhance stripping and evaporation of furfural and formic acid from reactor (1) the reactor (10) pressure is preferably higher than outside, e.g. in line (4), which pressure difference is provided by control valve (14). Preferably the outside pressure is from 0.5 to 2 bar absolute pressure, most preferably, for example, about atmospheric pressure i.e. about 1 bar absolute pressure.

The vapor flow is led to further processing, from which furfural (24) by distillation (20), and part of the formic acid (27) are recovered.

The process given in FIG. 1 following the output flow (5) including a control valve (15), flash, and vapor output (16), solid-liquid separator (17) is set up according to levulinic acid processes published in prior art. After rejection of solids (26), the liquids (25) are further treated to recover sulfuric acid (22) for reuse in the process and eventually levulinic acid.

The process is further presented through numerical values of mass balance clarifying the reactions taking place in the reactor. These values are given in table 1 below. As one of the main reactions, levulinic acid formation reaction proceeds producing as a side product, one mole of formic acid per one mole of formed levulinic acid. Simultaneously, furfural is also formed from the pentose components present in the feed.

According to lab tests the instantaneous recovery of furfural improves also levulinic acid formation when compared to the levulinic acid yield in the same reaction conditions without steam stripping.

TABLE 1

An example mass balance in accordance with laboratory test results of the present process. Flow/unit numbers correspond to reference numbers given in FIG. 1. The flow "water out" refers to water condensed from the processes taking place following the vapor line (4). In the table, ds refers to dry solids and '—' means 'not specified', and may have a case value, depending on levulinic acid purification process for example.

| | flow/unit | | | | | | | | | | |
|---|---|---|---|---|---|---|---|---|---|---|---|
| | 1 | 4 | 5 | 24 | water out | 26 | 2 | 3 | 10 | 16 | 25 |
| T, C.' | 130 | 180 | 180 | — | — | — | 130 | 190 | 180 | 100 | 100 |
| p, bara | 11 | 11 | 11 | — | — | — | 11 | 13.5 | 11 | 1 | — |
| kg/h | 100 | 60 | 122.5 | 3.4 | 42.5 | 40 | 22.5 | 50 | — | 12.3 | 70.3 |
| water w % | 50 | 91 | 65 | 0.2 | 98 | 50 | 65 | 100 | 75 | 90 | 64 |
| LA w % | 0 | 0 | 9 | 0 | 0 | 4 | — | 0 | 9 | 0 | 13 |
| FF w % | 0 | 5.8 | 0.1 | 99 | 0.0 | 0 | — | 0 | 0.1 | 0.2 | 0.0 |
| FA w % | 0 | 1.5 | 2.6 | 0 | 1.2 | 2 | — | 0 | 1.8 | 1.1 | 4.8 |
| $H_2SO_4$ w % | 0 | 0 | 4.5 | 0 | 0 | 0 | 24.5 | 0 | 4.5 | 0 | 4.6 |
| dry solids w % | 50 | 0 | 20 | 0 | 0 | 50 | — | 0 | 20 | 0 | — |
| hexoses w % of ds | 50 | 0 | 0 | 0 | 0 | 0 | 0 | 0 | — | 0 | 0 |
| pentoses w % of ds | 15 | 0 | 0 | 0 | 0 | 0 | 0 | 0 | — | 0 | 0 |

Experimental

The foregoing description provides non-limiting examples of some embodiments of the invention. It will be apparent to those skilled in the art that the invention is not restricted to details presented, but that the invention may be implemented in other equivalent means. Some of the features of the above-disclosed embodiments may be used to advantage without the use of other features.

Test Setup

Experimental conditions were set to measure if continuous steam stripping improved the levulinic acid yield when compared to the same reactor conditions without steam stripping. Furfural yield was measured and compared to the figures of a published process which have no steam stripping but flash after levulinic acid reactor. Percentages given herein refer to weight-%.

Reactor test conditions were the following:

| | |
|---|---|
| feed material | kraft pulp (Birch kraft pulp, 100 g dry/1000 g batch) |
| target temperature | 175° C. |
| balance pressure | ~12 . . . 16 barg |
| $H_2SO_4$ of feed | 4.51%-wt |
| feed slurry dry matter | 15%-wt |
| residence time at target temperature | 60-90 min |
| mixing | on |

Tests were conducted in a 2000 ml commercial batch reactor, which was equipped with a mixer (up to 1450 rpm), ceramic heating coils in jacket, (2.5 kW) and removable cooler coils in reactor.

First test (reference) was run without steam stripping. Both furfural and levulinic acid formed and accumulated in slurry. Next slurry was recovered, and furfural distilled off. In the second run, continuous steam stripping according to the present process was set up with following parameters:

The steam flow was provided by injecting 10 ml/min steam on into reactor and output of 10 ml/min vapor condensate. Stripping steam was heated at a heating unit comprising two separate heating coil units (1.7 kW/unit). A pump with 600 bar and max 20 ml/minutes was used as feed water pump into heating coils. The steam flow into reactor was opened when steam/water temperature was 200° C., and when reactor interior temperature reached 150° C.

Vapor output valve was tuned to keep condensate flow 1.1 times higher or as the same as steam/water input flow and keeping the reactor pressure steady ~10 barg.

Means for furfural recovery were further studied. Reaction conditions were otherwise kept the same, but two different furfural recovery methods were compared. The recovery of furfural by boiling the reactor was compared to recovery by different steam feeds, providing steam either 10% or 20% of the feed flow at boiling point. Reactor conditions were 170° C. and 8 barg, and stripping steam 250° C. and 25 barg. The aim was to demonstrate the differences in recovery, accepting that yield as such could be further improved by optimization. Results showing lower energy consumption for steam stripped than for boiled arrangements are compiled in table 1.

TABLE 1

Thermodynamic balance for steam stripping effect on furfural recovery from the reactor.

| Furfural recovery method | Furfural recovery % | Boiling and stripping energy usage, MW, for 1 kg/s feed |
|---|---|---|
| Boiling 20% of feed mass (no stripping steam) | 49 | 0.40 |
| Stripping steam 10% of feed flow at boiling point | 63 | 0.22 |
| Stripping steam 20% of feed flow at boiling point | 72 | 0.44 |

Conclusions

The levulinic acid yield (41.21%) was improved due to the stripping steam (test run 2) in comparison to the reference test without stripping steam (31.32 mol %, test run 1). However, the conversion to levulinic acid in the stripping steam reactor was not complete (residence time was too short). After continued conversion, the final levulinic acid conversions with birch Kraft pulp was 42.93 mol % with slurry from run 2 (with steam stripping) and 43.75 mol % with slurry from run 1 (without stripping steam). It may be concluded that practically the same levulinic acid yield was achieved with steam stripping and without steam stripping. However, with steam stripping conversion was faster.

With stripping steam the furfural yield into condensate was 42 wt-%, i.e. 65 mol-%. Compared to values reported in the literature, this is a good yield and proved the present process viable.

Even though the levulinic acid conversion was not optimal, this pair of experiments shows that the process setup enabling recovery of furfural from the same reactor as levulinic acid does not decrease the levulinic acid yield, as anticipated based on literature.

Conversion by steam stripping provided further benefits over reference (boiling) test. When the recovery of furfural by different steam inputs (10 and 20% of feed flow) was compared to recovery by boiling was, a clear result showing both enhanced yields and decrease in energy consumption for the present process.

In further experiments (results not shown) the levulinic acid conversion was improved with the present feed. Those results confirmed that the present process is applicable to combined levulinic acid and furfural production with yields comparable to those reported in the literature for separately optimized processes for each.

As such, the foregoing description shall be considered as merely illustrative of the principles disclosed herein, and not in limitation thereof. Hence, the scope of the invention is only restricted by the appended patent claims.

It will therefore be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

The invention claimed is:

1. A process for converting biomass into levulinic acid and furfural in one reactor, wherein process conditions in the reactor comprise:

temperature from 150 to 200° C.;
residence time at said temperature from 30 to 480 min;
$H_2SO_4$ content from 1 to 5%-wt of the feed; and continuous steam stripping,
wherein the levulinic acid is recovered from an output slurry of said reactor,
wherein furfural is continuously recovered from an output vapor flow of said reactor.

2. The process of claim 1, wherein the process conditions in said reactor comprise one or more of parameters selected from:
a pressure from 3 to 14 bar;
mixing;
dry matter from 5 to 30%-wt of the feed; and
aqueous slurry.

3. The process of claim 1, wherein a stripping steam temperature is about from 10° C. to 20° C. higher at a saturated balance pressure than the reactor temperature.

4. The process of claim 1, wherein a stripping steam pressure is lower than the saturated balance pressure and higher than the reactor pressure.

5. The process of claim 1, wherein the biomass comprises:
both hexoses and pentoses, with the hexose:pentose ratio being from 33:1 to 1:2.

6. The process of claim 1, wherein the residence time at the temperature from 150 to 200° C. is between 60 to 240 min.

7. The process of claim 1, wherein water is the sole solvent.

8. The process of claim 2, wherein a stripping steam temperature is about from 10° C. to 20° C. higher at a saturated balance pressure than the reactor temperature.

9. The process of claim 2, wherein a stripping steam pressure is lower than the saturated balance pressure and higher than the reactor pressure.

10. The process of claim 2, wherein water is the sole solvent.

11. The process of claim 6, wherein the residence time at the temperature from 150 to 200° C. is between 60 to 120 min.

12. The process of claim 1, comprising:
converting levulinic acid into products thereof, wherein the products of levulinic acid include resins, plasticizers, speciality chemicals, herbicides, or a fuel extender.

* * * * *